United States Patent [19]

Sherwin

[11] 4,135,381

[45] Jan. 23, 1979

[54] OXYGEN SENSOR TEMPERATURE MONITOR FOR AN ENGINE EXHAUST MONITORING SYSTEM

[75] Inventor: Walter M. Sherwin, Detroit, Mich.

[73] Assignee: General Motors Corporation, Detroit, Mich.

[21] Appl. No.: 814,660

[22] Filed: Jul. 11, 1977

[51] Int. Cl.$^2$ ............................................. G01N 31/22
[52] U.S. Cl. ...................................... 73/23; 73/117.3; 60/276
[58] Field of Search ................ 73/23, 116, 117.3, 344; 60/276; 123/32 EE; 204/1 Y, 195 S

[56] References Cited

U.S. PATENT DOCUMENTS

| 3,915,135 | 10/1975 | Kushida | 204/195 |
| 3,932,807 | 1/1976 | Wilson | 73/23 |
| 3,990,411 | 11/1976 | Toelle et al. | 60/276 |

Primary Examiner—Herbert Goldstein
Attorney, Agent, or Firm—Robert M. Sigler

[57] ABSTRACT

A vehicle engine includes an exhaust monitoring system with an exhaust mounted oxygen sensor and apparatus for processing the sensor output voltage into an exhaust constituent signal which may, for example, be used to control the air-fuel ratio of the engine fuel supply to a substantially stoichiometric ratio, the apparatus including a low pass filter which suppresses components of the signal greater in frequency than a predetermined cutoff frequency. An alternating voltage generator effective to generate a square wave of at least the cutoff frequency is connected through a reference impedance, a capacitor and the oxygen sensor in series to ground, thus creating a voltage divider with an output between the reference impedance and the sensor internal impedance, the voltage at the output having a peak-to-peak amplitude which varies inversely with sensor temperature. The voltage at the output is provided to a peak detector, which generates therefrom a signal representing the temperature of the oxygen sensor. The low pass filter in the closed loop fuel control and the capacitor protect the exhaust constituent signal from distortion by the alternating voltage.

2 Claims, 4 Drawing Figures

WAVE FORMS, SENSOR IMPEDANCE = 30 KΩ (COLD)

WAVE FORMS, SENSOR IMPEDANCE = 4 KΩ (HOT)

OXYGEN SENSOR TEMPERATURE MONITOR FOR AN ENGINE EXHAUST MONITORING SYSTEM

BACKGROUND OF THE INVENTION

This invention relates to engine exhaust monitoring systems for vehicle mounted internal combustion engines, in particular such systems using oxygen sensors of the solid electrolyte type in the engine exhaust system. Such systems are useful in providing a signal indicative of air-fuel ratio to engine fuel controls in a manner well known in the art.

It is well known and documented in the prior art that the output voltage of such sensors is affected by the sensor temperature. It might be advantageous, therefore, to include, in some closed loop fuel control systems, apparatus for monitoring sensor temperature and generating an output signal in response thereto. For example, in a system relying on the heat of engine exhaust gases to heat the sensor to its normal operating temperature, such monitoring apparatus could compare the sensor temperature signal to a reference and signal when the operating temperature has been reached. In a system with an electrically heated sensor, such monitoring apparatus can provide a sensor temperature feedback control signal to maintain a desired sensor temperature. In addition, it might be possible to use the signal from such sensor temperature monitoring apparatus to compensate the sensor's output signal as its temperature changes.

To be most useful, such temperature monitoring apparatus should not require any changes in the sensor itself, such as the inclusion of extra temperature measuring elements or extra connection terminals. In addition, such apparatus should ideally require no further modifications to the vehicle exhaust system, such as the addition of a temperature measuring element in the vicinity of the oxygen sensor. Instead, the temperature monitoring apparatus should be of the type which connects to the normal output terminal or terminals of the oxygen sensor so that it can be used with any prospective sensor design and, in fact, could be included within the closed loop electronic package. On the other hand, the temperature monitoring apparatus must not affect the operation of the closed loop system in an unfavorable manner by distorting the output signal of the oxygen sensor or interacting with the rest of the closed loop system in an undesirable manner.

SUMMARY OF THE INVENTION

This invention provides oxygen sensor temperature monitoring apparatus which uses the internal impedance of the oxygen sensor in a voltage divider with a reference impedance. The internal sensor impedance, as measured between its output terminal and ground, is well known in the prior art to vary inversely with temperature: varying from possibly several megohms at normal ambient atmospheric temperature to a few kilohms at the elevated temperatures typical of engine exhaust gases.

A voltage is applied to the voltage divider comprising the reference impedance and the sensor internal impedance. In order that this voltage not affect the exhaust constituent signal, the voltage comprises an alternating voltage such as a square wave of a frequency greater than the closed loop system is designed to respond to. Some closed loop systems are provided with low pass filter apparatus to reject high frequency noise in the sensor signal. If so, the shape and frequency of the alternating voltage chosen so that it is effectively filtered out of the sensor signal by the low pass filter apparatus. If such low pass filter apparatus is not already included in the closed loop system, it is added. Finally, a capacitor is included between the reference impedance and sensor to block any constant voltage bias in the alternating voltage from the sensor output where, if it were present, it might be integrated by the low pass filter means in the closed loop fuel control system to cause the closed loop fuel control system to slew in one direction or the other.

The voltage at the junction of the reference impedance and capacitor is supplied to peak detecting apparatus which generates an output signal varying with the peak-to-peak voltage at said junction. This output comprises the sensor temperature signal, which may be used for any of the purposes described above.

It can be seen that this invention has particular application to digital electronic systems, since a square wave generator or pulse generator is normally already present in such systems and is easily modified to produce square clock pulses of the required frequency.

Further details and advantages of this invention will be apparent from the accompanying drawings and following description of a preferred embodiment.

DESCRIPTION OF THE PREFERRED EMBODIMENT

Figure 1:
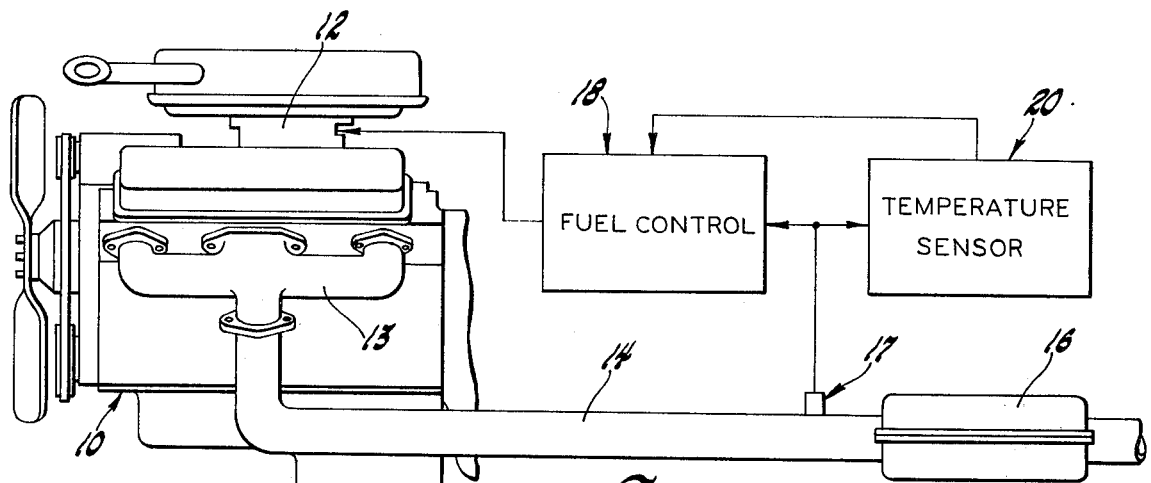
FIG. 1 is a schematic diagram of an embodiment of this invention in a suitable environment.

Referring to FIG. 1 an engine 10 is adapted for use in a motor vehicle and is understood to be mounted on such vehicle, even though, for convenience, no such vehicle is shown. Engine 10 has fuel metering apparatus 12 which mixes air with a fluid fuel capable of being oxidized by the oxygen in the air in an environment where energy is released at least partly in the form of mechanical work done on parts of engine 10 to turn an output shaft thereof. Fuel metering apparatus 12 may be a carburetor, a fuel injection and air induction system or similar apparatus known in the art. An exhaust manifold 13 and exhaust pipe 14 are provided for the conduction of combustion products away from the engine 10 and dispersal to the atmosphere.

In order to reduce the concentration of certain compounds, such as unburned hydrocarbons, carbon monoxide and oxides of nitrogen, in the exhaust gases dispersed to the atmosphere from exhaust pipe 14, a catalytic converter 16 is provided with exhaust pipe 14 for those exhaust gases to flow through before dispersal to the atmosphere. Catalytic converter 16, of which only the outer case is shown, is the type which contains a suitably mounted catalyst which is effective to simultaneously oxidize hydrocarbons and carbon monoxides and reduce oxides of nitrogen when provided with exhaust gases containing oxygen and oxidizable substances in a substantially stoichiometric ratio. Such converters are well known and need not be described in detail. In order to insure that the ratio of such substances in the exhaust gases remains at stoichiometry, an oxygen sensor 17 of the type described above is provided in exhaust pipe 14 upstream from catalytic converter 16. An example of such a sensor is shown in the U.S. Pat. to Birgett et al., No. 3,844,920. The output signal of oxygen sensor 17 is supplied to a fuel control, indicated generally at 18 which generates an air-fuel ratio controlling signal, which may be applied to fuel metering apparatus 12. Such systems as that described to this point are well known in the prior art and need not be described further in this application except for a few particular features which have an important bearing on this invention.

It can be seen in FIG. 1 that the output of oxygen sensor 17 is also supplied to temperature sensor apparatus 20, which generates an output signal that varies with sensor temperature and that may be applied to fuel control 18 in some manner. It should be noted at this point, lest the reader be misguided by the over-simplified connections shown in FIG. 1, that the signal from sensor 17 applied directly to fuel control 18 is not identical with the signal supplied from sensor 17 to temperature sensor apparatus 20. As will be evident from FIG. 2 and the following description, the sensor is being used in two different ways simultaneously by the fuel control 18 and temperature sensor apparatus 20, as will be shown in greater detail later in this description.

Figure 2:
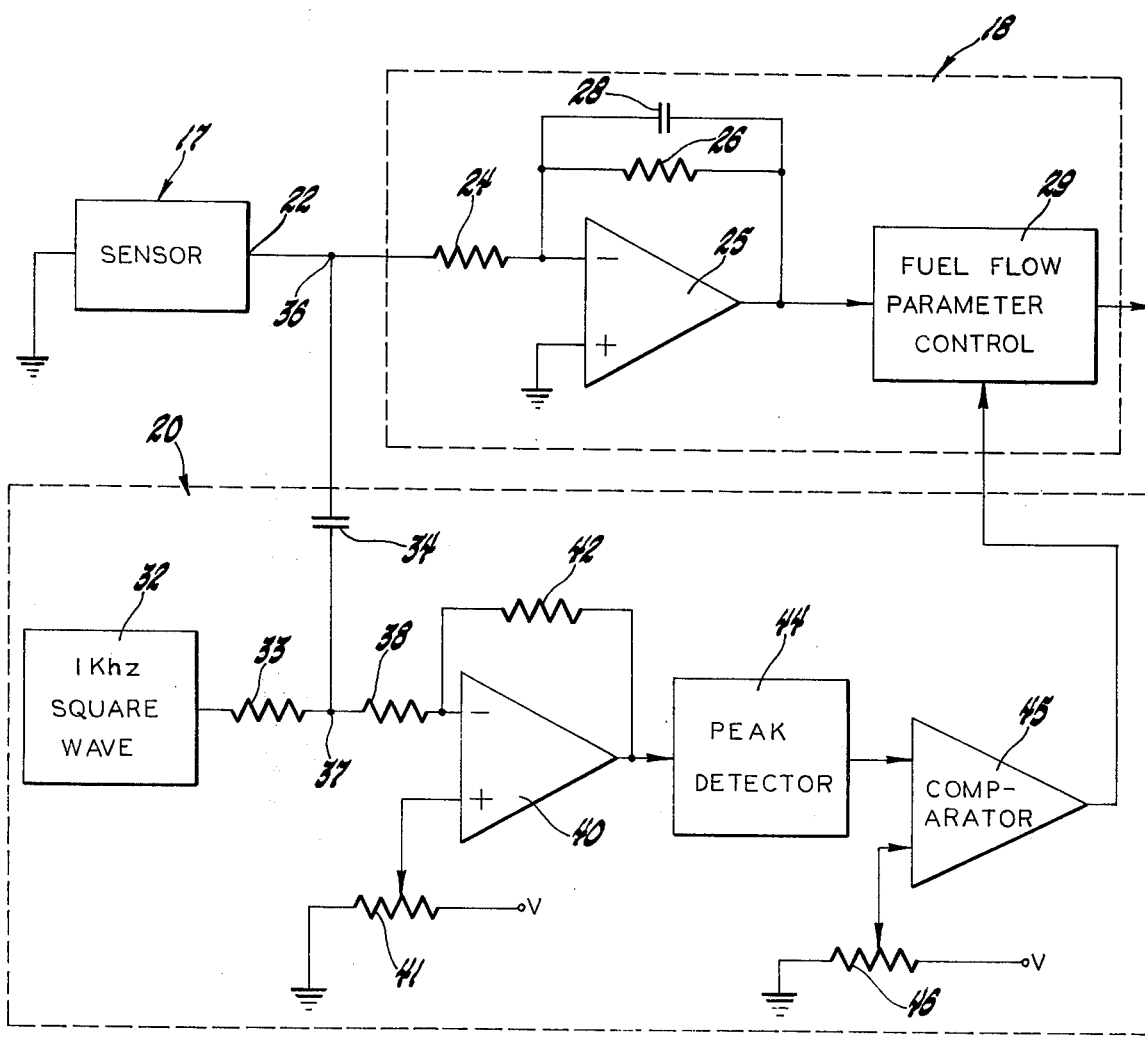
FIG. 2 is a circuit and block diagram of an embodiment of this invention for use in the environment of FIG. 1.

Referring to FIG. 2, oxygen sensor 17 is a two-terminal device having one terminal grounded through the sensor body to the exhaust pipe and vehicle body in the normal manner and the other terminal 22 connected through a resistor 24 to the negative input of an operational amplifier or op-amp 25, the non-inverting input of which is grounded and the output of which is fed back to the inverting input through the parallel combination of a resistor 26 and capacitor 28. The output of op-amp 25 is also supplied to a fuel flow parameter control 29, which generates the air-fuel ratio signal for application to fuel metering apparatus 12 in any known manner. Op-amp 25 and its associated resistors 24 and 26 and capacitor 28 comprise a low pass filter or integrator with a predetermined cutoff frequency for use with fuel flow parameter control 29 in fuel control 18. The representation of this circuitry is, of course, somewhat schematic, with only the low pass filter apparatus being shown in actual circuit form. In addition, the low pass filter apparatus is shown as being located at the input of the fuel control 18, whereas in practice it need not be necessarily in that position. However, the low pass filter apparatus has been separated from the remainder of the fuel control 18 in FIG. 2 since this is the portion of the fuel control 18 which is of primary importance in describing the preferred embodiment of this invention.

The low pass filter circuitry is often suggested for fuel controls of this type to filter out unwanted high frequency noise. In practice, due to the dynamics of engine operation with fuel controls of this type, most desirable information from the oxygen sensor has a fairly low frequency content — usually well below 1,000 hertz. Therefore frequency content of this frequency and greater may be filtered out to improve the signal to noise ratio. Although the frequency of 1,000 hertz is used in this embodiment, it may be found for a particular engine that a lower or higher frequency is more appropriate: the particular frequency of 1,000 hertz is not intended as a limitation of this invention.

Also, it is understood that no filter has a perfectly sharp cutoff. The filter apparatus shown will cause a gradual attenuation in amplitude as frequency increases. However, it is said to have a predetermined cutoff frequency in the sense that signals of this frequency or above are attenuated sufficiently with respect to the signals of interest, which may be of much lower frequency, that they are practically negligible; the low pass filter may have a break frequency far below the predetermined cutoff frequency: at 100 hertz, for example.

An alternating voltage generator 32, which may be an already existing pulse generator in a digital fuel control system, provides, in this embodiment, a one kilohertz square wave with a constant peak-to-peak amplitude of ground to five volts. Alternating voltage generator 32 is connected through a reference impedance 33, in this embodiment a resistor, and a capacitor 34 in series to the junction 36 of sensor 17 and closed loop fuel control 18, which junction 36 is electrically equivalent to output terminal 22 of sensor 17. The junction 37 of impedance 33 and capacitor 34 is connected through a resistor 38 to the inverting input of an op-amp 40, the non-inverting input of which is connected to a variable resistor 41 connected as a voltage divider between a supply voltage V and ground and the output of which is fed back through a resistor 42 to the inverting input. The output of op-amp 40 is also connected to peak detector apparatus, the output of which is a signal representing the temperature of sensor 17. The output of peak detector 44 may be supplied to one input of a comparator 45, the other input of which is connected to a variable resistor 46 connected as a voltage divider between the reference voltage V and ground. The output of comparator 45 is shown, in this embodiment, as being supplied to fuel flow parameter control 29.

In operation, reference impedance 33 forms a voltage divider for the peak-to-peak voltage of the square wave with the internal impedance of sensor 17 between alternating voltage generator 32 and ground. The output of this voltage divider, which is taken in this embodiment at junction 37, is a modulated alternating voltage, the peak-to-peak amplitude of which varies with the internal impedance and therefore the temperature of sensor 17. The presence of capacitor 34 causes a somewhat different wave form to be present at junction 36, but with similar peak-to-peak amplitude.

Figure 4:
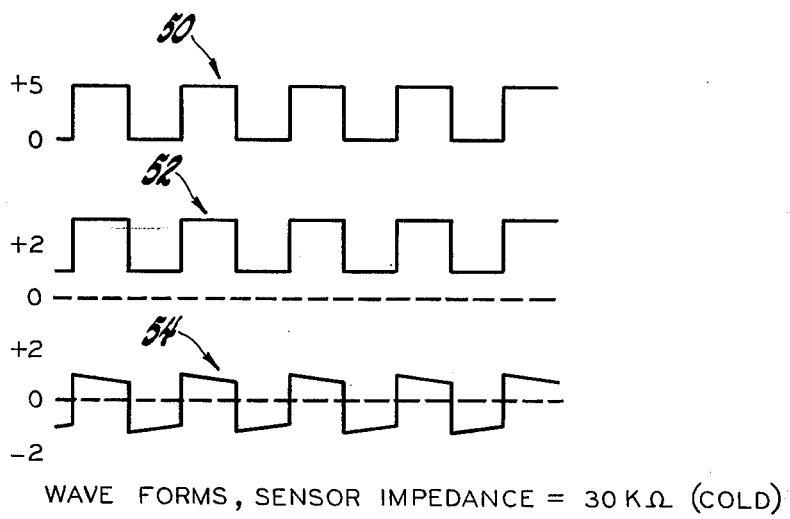
FIG. 4 shows a series of wave forms of voltage versus time at selected points in the embodiment of FIG. 2.
Figure 4:
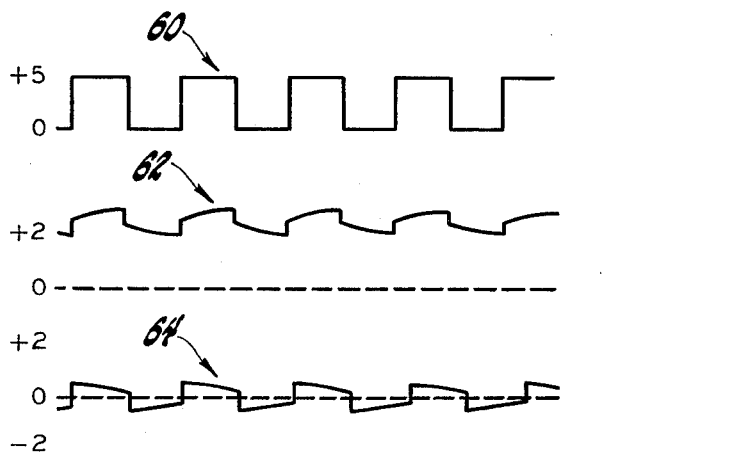

The wave forms for junctions 36 and 37 are shown for a hot and cold sensor in FIG. 4. For a sensor impedance of 30 kilohms, which represents a cooler sensor, wave form 50 is the output of AC generator 32, wave form 52 is the voltage at junction 37 and wave form 54 is the voltage at junction 36. For a sensor impedance of four kilohms, which represents a hotter sensor, wave form 60 represents the output of AC generator 32, wave form 62 represents the voltage at junction 37 and wave form 64 represents the voltage at junction 36.

It can be seen from the wave forms of FIG. 4 that, given a square wave 50, 60 of constant peak-to-peak amplitude, the voltage at junction 37 has a peak-to-peak amplitude which decreases as the sensor impedance decreases or as sensor temperature increases. The voltage at junction 36 shows a similar decrease in peak-to-peak amplitude with sensor impedance; but, due to the effect of the capacitor 34, it has a slightly different shape and has no DC component with reference to ground.

The low pass filter apparatus comprising op-amp 25 and its associated passive elements is designed with a cutoff frequency such that one kilohertz is effectively suppressed and is not passed in the fuel control 18. Thus the square wave output of AC generator 32 is not passed as a square wave through fuel control 18. In addition, since capacitor 34 blocks any constant voltage bias with reference to ground from generator 32, low pass filter 25, which also acts as an integrator, will produce an integral of zero from the wave form at junction 36 as received through capacitor 34. Thus the square wave output of generator 32 has no effect on fuel control 18.

The voltage at the junction 37 is amplified in amplifier 40 and supplied to peak detector apparatus 44. Peak detector apparatus 44 is of the type which senses the peak-to-peak amplitude of the wave form supplied to it and generates an output signal varying with that peak-to-peak amplitude. For example, it may include a rectifier and low pass filter to produce as an output a unidirectional or DC voltage which substantially follows the peak-to-peak voltage of junction 37. This voltage thus also follows the temperature of sensor 17. Other types of peak detectors are known and could be used in this invention.

In this embodiment, the output of peak detector 44 is compared with a reference voltage set by variable resistor 46, which represents the minimum normal operating temperature of sensor 17. The output of comparator 45 can then be supplied to fuel flow parameter control 29 to switch control of fuel metering apparatus 12 to the fuel control 18 only when the minimum normal operating temperature is reached.

Figure 3:
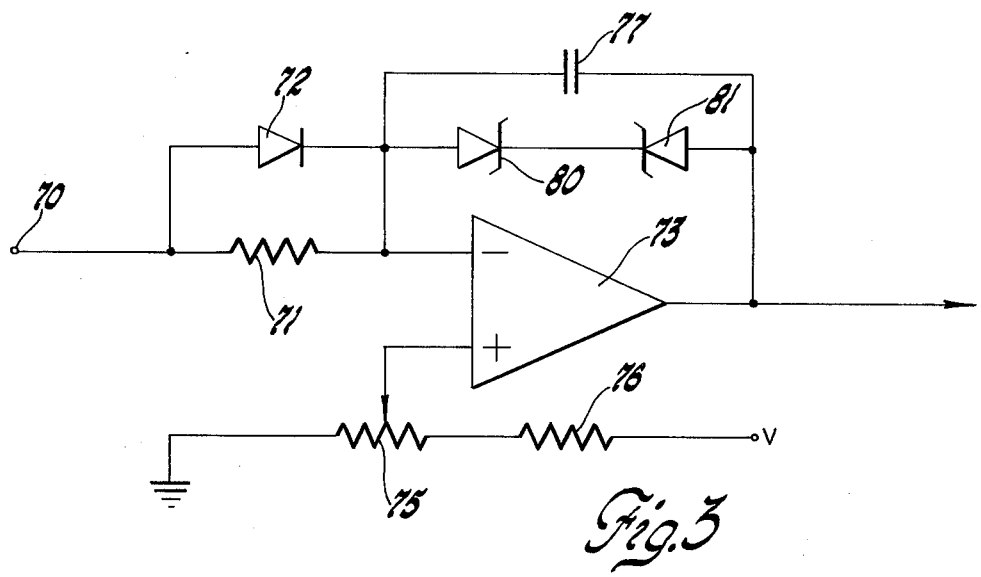
FIG. 3 is a circuit diagram of a portion of the embodiment shown in FIG. 2.

FIG. 3 shows an embodiment of circuitry which has been found to effectively combine the functions of op-amp 40, peak detector 44 and comparator 45 and may be substituted therefore in the embodiment of FIG. 2 beginning at junction 37. Input terminal 70 of the circuit of FIG. 3 is connected to junction 37 in FIG. 2 and is itself connected through a resistor 71 and diode 72 to the inverting input of an op-amp 73, the non-inverting input of which is connected to a variable resistor 75 connected in voltage divider configuration comprising, in series, a source of potential V, a resistor 76, variable resistor 75 and ground. The output of op-amp 73 is fed back through a capacitor 77 to the inverting input; and a pair of zener diodes 80, 81 is connected back-to-back across capacitor 77.

In operation, op-amp 73 and capacitor 77 comprise an integrator which integrates downward to a low level whenever the peak-to-peak voltage at terminal 70 exceeds the forward voltage drop of diode 72 and stays at the low value until the peak-to-peak voltage at terminal 70 falls below the forward voltage drop of diode 72, which occurs with a hot sensor. When the latter occurs, integrator 73 integrates upward, as determined by resistors 75 and 76, to a high level, where it stays until the peak-to-peak voltage at terminal 70 once again exceeds the voltage drop of diode 72. Thus the circuit approximates the peak detector and comparator shown in FIG. 2 Back-to back zener diodes 80 and 81 are voltage limiters which are not essential for the operation of the circuit but are useful in some applications in protecting circuit elements beyond the output of op-amp 73.

In this embodiment, circuit element values for the circuit of FIG. 3 are: resistor 71, 100K; resistor 75, 5K; resistor 76, 20K; capacitor 77, 0.5 Mf.

The embodiment described above is a preferred embodiment only; equivalent embodiments will occur to those skilled in the art upon reading this description. Therefore this invention should be limited only by the claims which follows The embodiments of the invention in which an exclusive property or privilege is claimed are defined as follows:

1. Temperature monitoring apparatus for use in a vehicle engine exhaust constituent monitoring system of the type including a sensor exposed to engine exhaust and effective to generate a voltage varying with the concentration of an exhaust constituent, the sensor further being characterized by an internal impedance varying with sensor temperature, and means responsive to the sensor voltage for generating an exhaust constituent signal therefrom, said means including low pass filter means characterized by a predetermined cutoff frequency for suppressing components of the sensor voltage having frequencies greater than said predetermined cutoff frequency, the apparatus comprising, in combination:

a capacitor;

a reference impedance coupled in series with the sensor and the capacitor therebetween to form a voltage divider with the sensor internal impedance, the voltage divider having an output between the reference impedance and sensor internal impedance;

means for generating an alternating voltage of constant peak-to-peak amplitude and a frequency greater than the predetermined cutoff frequency of the exhaust constituent signal generating means and applying the alternating voltage across the voltage divider, whereby the voltage divider produces at its output a modulated alternating voltage having a peak-to-peak amplitude varying with the sensor internal impedance and therefore providing an indication of sensor temperature and further having a frequency greater than the predetermined cutoff frequency, the exhaust constituent signal being isolated from the alternating voltage by the low pass filter means and from any superimposed unidirectional bias in the alternating voltage by the capacitor; and peak detector means responsive to the peak-to-peak amplitude of the modulated alternating voltage and generating a sensor temperature signal therefrom.

2. In a vehicle engine having an exhaust conduit, an oxygen sensor in the exhaust conduit exposed to the engine exhaust therein, the oxygen sensor being of the type generating a voltage signal indicative of oxygen concentration in the engine exhaust and further exhibiting an internal impedance varying inversely with sensor temperature, and means responsive to said voltage signal to generate an exhaust oxygen signal therefrom, said means including low pass filter means having a predetermined cutoff frequency, the improvement comprising:

a capacitor;

a reference impedance connected through the capacitor to the oxygen sensor in series with the sensor internal impedance, the reference impedance, capacitor and sensor forming a voltage divider with an output between the reference impedance and capacitor;

a square wave voltage generator effective to generate a square wave voltage having a constant peak-topeak amplitude a frequency of at least the cutoff frequency, the square wave voltage generator being connected across the voltage divider, whereby the voltage at the voltage divider output has a peak-to-peak amplitude which varies directly with the sensor internal impedance and therefore inversely with the sensor temperature, the exhaust oxygen signal being isolated from the square wave voltage by the low pass filter means and from any unidirectional DC bias voltage from the square wave voltage generator by the capacitor; and peak detector means connected to the voltage divider output and responsive to the peak-to-peak amplitude of the voltage thereon to generate a sensor temperature signal in accordance therewith.

* * * * *